United States Patent [19]

Meyer et al.

[11] Patent Number: 4,840,815

[45] Date of Patent: Jun. 20, 1989

[54] LOW CALORIC ALKYL GLYCOSIDE FATTY ACID POLYESTER FAT SUBSTITUTES

[75] Inventors: Richard S. Meyer; Jeffrey M. Root, both of Tacoma; Michael L. Campbell, Kent; Daryl B. Winter, Seattle, all of Wash.

[73] Assignee: Curtice-Burns, Inc., Rochester, N.Y.

[21] Appl. No.: 122,188

[22] Filed: Nov. 18, 1987

Related U.S. Application Data

[63] Continuation-in-part of Ser. No. 49,625, May 13, 1987, abandoned.

[51] Int. Cl.$^4$ .............................................. A23D 5/00
[52] U.S. Cl. .................................... 426/611; 426/601; 426/804; 536/4.1
[58] Field of Search ..................... 426/601, 611, 804; 536/4.1

[56] References Cited

U.S. PATENT DOCUMENTS

| | | | |
|---|---|---|---|
| 3,597,417 | 8/1971 | Myhre | 536/119 |
| 3,598,865 | 8/1971 | Lew | 536/18.6 |
| 4,005,195 | 1/1977 | Jandacek | 514/23 |

Primary Examiner—Donald E. Czaja
Assistant Examiner—Celine T. Callahan
Attorney, Agent, or Firm—Christensen, O'Connor, Johnson & Kindness

[57] ABSTRACT

Alkyl glycoside fatty acid polyesters having at least four fatty acid ester groups being both saturated and unsaturated and having 4 to 24 carbon atoms wherein the alkyl glycoside moiety comprises a saccharide and an alkyl portion are suitable for use as a low calorie fat substitute food composition.

7 Claims, No Drawings

LOW CALORIC ALKYL GLYCOSIDE FATTY ACID POLYESTER FAT SUBSTITUTES

CROSS-REFERENCE TO RELATED APPLICATION

This is a continuation-in-part of prior application Ser. No. 049,625, filed May 13, 1987, now abandoned, the benefit of which filling date is hereby claimed under 35 U.S.C. 120.

TECHNICAL FIELD

This invention relates to a method for producing alkyl glycoside fatty acid polyester fat substitutes and the use thereof in food compositions.

BACKGROUND OF THE INVENTION

One of the most common nutritional problems in the United States today is obesity. In general, obesity results from the consumption of more calories than are expended. Fats contribute from 30% to 40% of the total calories consumed by most Americans. Consumption of fat is related to many disease states, such as heart disease. Successful reduction of fat consumption has not been achieved because of the dietary habits of the traditional American. Therefore, the search for fat substitutes or low-calorie fats has attracted considerable attention in recent years.

Among the possible low-calorie fats or fat substituents synthesized to date are: sugar polyesters, sugar alcohol polyesters such as sucrose polyesters (SPE), polyglycerol esters, neopentyl-type alcohol esters, glycerol dialkyl ethers, triglyceride esters of alpha substituted carboxylic acids, diglyceride esters of short-chain dibasic acids, trialkoxytricarballyate, polydextrose, palatinose, polygalactose, N-oil (tapioca dextrin), microbiologically derived products, nonabsorbable synthetic polymers with properties similar to edible oil, tree-derived products, low-metabolized natural fats and oils, bipolymers, branched polysaccharides and jojoba oil. Many of these are reviewed by Hamm, *J. Food Sci.* 49, 419 (1984).

Alkyl glycoside compositions are known in the art to be useful as detergents, gelling agents, and as food emulsifiers. Baak, U.S. Pat. No. 3,772,269, discloses a method for making alkyl glycosides by reacting monosaccharides with long chain monohydric alcohols in the presence of an acid catalyst.

Gibbons, U.S. Pat. No. 2,759,923, discloses a method for esterification of glucosides with fatty acids in the presence of an alkaline catalyst. Tetraester alkyl glycosides are produced according to the method of Gibbons at temperatures above 200° C. and are suitable for use as drying oils in products such as varnishes.

Gibbons et al., U.S. Pat. No. 2,931,797, discloses mixed methyl glucosideglycerol partial esters produced by alcoholysis of triglycerides with methyl glucoside. These partial esters are suitable for use as nonionic emulsifiers.

Myhre, U.S. Pat. No. 3,597,417, discloses a process for preparing fatty acid esters of sugar glycosides. Myhre first reacts a sugar glycoside with the methyl ester of a short chain acid to produce the sugar glycoside short chain esters. These sugar glycoside short chain esters are then reacted with a long chain fatty acid ester in the presence of an alkali metal alkoxide to produce the sugar glycoside fatty acid ester. Small amounts of these sugar glycoside esters are blended into the shortening component of cake mixes to improve the baking characteristics of the cake mix.

SUMMARY OF THE INVENTION

The present invention provides a significantly improved process for the manufacture of alkyl glycoside fatty acid polyesters. The process consists of reacting a reducing saccharide with a monohydric alcohol thereby forming an alkyl glycoside. The hydroxyl groups of these alkyl glycosides are then esterified to form a lower acyl ester alkyl glycoside. The lower acyl ester alkyl glycoside is then admixed with a fatty acid lower acyl ester and an alkali metal catalyst thereby forming a reaction mixture which is maintained at a temperature of from about 100° C. to about 125° C. This reaction mixture is maintained at that temperature for a period of up to three hours. All components of the reaction mixture are thoroughly dried prior to their combination and are kept dry during the period of the reaction by contacting the surface of the reaction mixture with a dry inert gas, such as nitrogen. The fatty acid lower acyl esters and lower acyl alkyl glycosides are combined in molar ratios of from about 4:1 to about 15:1. Either homogeneous or heterogeneous fatty acids lower alkyl esters can be added to their reaction mixture and, in general, the fatty acid portion of the fatty acid lower acyl ester is a fatty acid having from about 4 to about 24 carbon atoms. The alkyl glycosides of the reaction mixture are the product of the reaction of reducing mono-, di- and trisaccharides with monohydric alcohols having from 1 to 24 carbon atoms. The alkyl glycoside fatty acid polyesters produced by this process and having at least four fatty acid ester groups are suitable for use as a fat substitute food composition.

Other fat substitute food compositions of the present invention include food compositions containing both fat and nonfat ingredients, wherein from about five to about 95% of the fat ingredients comprise a low melting point alkyl glycoside fatty acid polyester compound and an effective amount of a high melting point alkyl glycoside fatty acid polyester sufficient to prevent anal leakage of the compound.

DETAILED DESCRIPTION OF THE INVENTION

In its broadest sense, the process of the present invention for producing alkyl glycoside fatty acid polyesters is a solvent-free, single step synthesis in which the reactants and catalysts are combined prior to heating. Additionally, a vaccum is drawn over the reaction mixture while it is being heated to the reaction temperature and during the time it is maintained at a reaction temperature. Finally, all reagents and implements of the reaction are scrupulously dried to prevent any saponification of any esters present in the reaction mixture.

The alkyl glycoside starting materials for the present invention include alkyl glycosides of mono-, di-, and trisaccharides. These alkyl glycosides can be produced by procedures well known in the art, or purchased from commercial sources. Methods for producing alkyl glycosides from reducing sugars and monohydric alcohols having from 8 to 25 carbons are described by Lew, U.S. Pat. No. 3,722,269, and Klahr et al., U.S. Pat. No. 4,349,669. Examples of suitable reducing saccharides that can be utilized as starting materials are monosaccharides such as fructose, glucose, galactose, mannose, ribulose, rhamnose, xylulose, xylose, ribose, and arabinose. A preferred monosaccharide is glucose. Suitable disaccharides for use in conjunction with the method of the present invention include melibiose, lactose, maltose, and cellobiose. The most preferred disaccharides is lactose. Trisaccharides utilized in accordance with the method of the present invention include 4'-galactosyl lactose and reducing trisaccharides of galactose, mannose, glucose, and fructose. The most preferred reducing trisaccharide is 4'-galactosyl lactose. By 4'-galactosyl lactose as used herein is means O-$\beta$-D-galactopyranosyl-(1--4)-O-$\beta$-D-galactopyranosyl-(1--4)-D-glucose.

Alcohols suitable for forming alkyl glycosides with reducing saccharides include: alkyl, aryl, alkaryl, aralkyl, heteroalkyl, heteroaryl, and monohydric alcohols. The preferred alcohol starting material suitable for production of the alkyl glycosides are alkyl alchohols having from 1 to 24 carbons. The most preferred alcohols are straight chain, fully saturated monohydric alcohols having from 1 to 18 carbons. These include by way of illustration the following alcohols: methyl, ethyl, n-propyl, n-butyl, n-pentyl, n-octyl, n-decyl, n-dodecyl, n-tetradecyl, n-hexadecyl, and n-octadecyl. The very most preferred alcohols are methyl, ethanol and propanol.

In order to be usable in accordance with the method of the present invention, hydroxyl groups on the alkyl glycosides are esterified to form lower acyl ester alkyl glycosides. By lower acyl is meant an acyl group having six or fewer carbon atoms. Preferably, acetyl and propionyl esters are employed. These lower acyl ester alkyl glycosides are formed so that all available hydroxyl groups are converted to esters by conventional methods. An example of a conventional method of esterification that can be employed, is the method of Linstead, R. P.; Rutenberg, A.; Dauben, W. G.; and Evans, W. L. *J. Am. Chem. Soc.*, 62:3260 (1940).

After synthesis of the alkyl glycoside lower acyl esters, they are reacted with suitable fatty acids lower alkyl esters by the procedure described below.

Suitable fatty acid lower alkyl esters produced for use in conjunction with the method of the present invention are made from fatty acids having from 4 to 24 carbon atoms. Examples of fatty acids usable in accordance with the present invention are butyric, caprylic, capric, lauric, myristic, myristoleic, palmitic, palmitoleic, stearic, oleic, ricinoleic, linoleic, linolenic, oleosteric, arachidic, behenic, erucic, arachidonic and lignoceric. Pure fatty acids or naturally occurring fats and oils can serve as a source of the fatty acid components for alkyl glycoside fatty acid polyesters produced in accordance with the present invention. Suitable fats and oils include coconut oil, palm kernel oil, babassu oils, corn oil, soybean oil, safflower seed oil, peanut oil, olive oil, palm oil, sunflower seed oil, sesame seed oil and cotton seed oil. Mixtures of fatty acids derived from soybean, safflower, corn, peanut and cotton seed oils are especially preferred because they contain froma bout 14 to 18 carbon atoms. In general, it is preferred that the fatty acids range from 14 to 18 carbon atoms because they do not volatilize at the interesterification temperatures. To be suitable for use in accordance with this invention, the fatty acids are converted to lower alkyl fatty acid esters by conventional esterification procedures prior to reacting with a suitable alkyl glycoside lower alkyl ester. Examples of suitable lower alkyl fatty acid esters include, but are not limited to: myristate fatty acid methyl ester (FAME), palmitate FAME, palmitoleate FAME, stearate FAME, oleate FAME, linoleate FAME, myristate fatty acid ethyl ester (FAEE) palmitate FAEE, palmitoleate FAEE, stearate FAEE, oleate FAEE, and linoleate FAEE.

Prior to combining the reactants, both the lower alkyl fatty acid ester and the alkyl glycoside lower alkyl ester are thoroughly dried by conventional procedures, for example, vacuum drying over anhydrous sodium or magnesium sulfate, followed by dry nitrogen purging. The substantially anhydrous lower alkyl fatty acid ester and alkyl glycoside lower alkyl ester are combined in mole ratios of at least 4:1, and preferably from 6:1 to 15:1, depending on the alkyl glycoside lower alkyl esters. To achieve high yields in accordance with the present invention, a catalyst is combined with the reactants prior to heating. Suitable catalysts include the alkali metal catalysts. Sodium and potassium are the most preferred of the alkali metals. Catalysts can be used in amounts up to 5% by weight but are preferably used in amounts on the order of 2% by weight.

As mentioned above, in order to achieve the high yields possible in accordance with the present invention, all components of the reaction mixture must be combined at room or slightly elevated temperature. It is preferred that the reaction mixture be heated to a reaction temperature gradually, preferably a heating rate no greater than 3° C. per minute. Preferably reaction temperatures range from 100° C. to 125° C., while the temperature range of 105° C. to 115° C. is most preferred. During the heating and maintenance of the reaction temperature, the area over the reaction vessel is evacuated and flooded with a dry, inert atmosphere. The inert atmosphere can comprise any inert gas, but nitrogen is preferred because of its cost and availability. In order to obtain the yields established in accordance with the present invention, the vacuum pulled over the reaction mixture must be less than 15 torr and, preferably, in the range of from 0 to 8 torr. Under these conditions, a 95% to 99% yield can be achieved while maintaining the reaction mixture of the reaction temperature for only about two to two and one-half hours.

Alkyl glycoside fatty acid polyesters produced in accordance with the present invention include: methyl glucoside tetraoleate, ethyl glucoside tetraoleate, the ethyl glucoside fatty acid polyester made from peanut oil FAME, ethyl galactoside fatty acid polyester made from peanut oil FAEE, n-octyl glucoside fatty acid polyester made from peanut oil FAEE, ethyl lactoside fatty acid polyester made from peanut oil FAME, and ethyl 4'-galactosyl lactoside fatty acid polyester.

By alkyl glycoside fatty acid polyesters as used in this invention is meant alkyl glycosides in which four or more of the alkyl glycoside hydroxyl groups have been esterified with a fatty acid. Yields reported for alkyl glycoside fatty acid polyesters in this invention are based on n-1 or more alkyl glycoside hydroxyl groups being esterified with a fatty acid, where n is the maximum number of ester bonds possible for a given alkyl glycoside.

Both homogeneous and heterogeneous alkyl glycoside fatty acid polyesters can be produced in accordance with the method of this invention. Examples of preferred homogenous alkyl glycoside fatty acid polyesters are: methyl glucoside tetraoleate, ethyl glucoside tetraoleate, ethyl galactoside tetrapalmitate, and ethyl lactoside heptastearate. Heterogeneous alkyl glycoside fatty acid polyesters are produced by blending two or more fatty acid lower alkyl fatty acid esters in the reaction mixtures in predetermined ratios. For example, ethyl lactoside heptaacetate, ethyl oleate and ethyl palmitate can be added to the reaction mixture in a ratio of 1:6:4 to produce a heteropolyester of ethyl lactoside. Alternatively, alkyl glycoside lower acyl esters can be reacted with heterogeneous mixtures of fatty acid lower alkyl esters produced from natural oils such as peanut oil to produce heterogeneous alkyl glycoside fatty acid polyesters. An example of such a compound is ethyl 4'-galactosyl lactoside fatty acid polyester made from peanut oil FAME.

Alkyl glycoside fatty acid polyesters produced by the above procedures are suitable for use as fat substitute food compositions. Preferred fat substitute food compositions are composed of both nonfat ingredients and fat ingredients wherein from about 5% to about 95% of the total fat ingredients are the alkyl glycoside fatty acid polyesters of the present invention in which alkyl glycoside is esterified to at least four fatty acids. The alkyl glycoside portion of the alkyl glycoside fatty acid polyester fat substitute food composition is the reaction product of a reducing mono-, di- and trisaccharide with a monohydric alcohol having from 2 to 24 carbons. The preferred alkyl glycoside portions are the reaction product of glucose, galactose, lactose and maltose with ethanol and propanol. The fatty acid portion of the alkyl glycoside fatty acid polyester fat substitute food composition is a fatty acid having from 4 to 24 carbons. Preferred fatty acids have from 12 to 18 carbons.

It has been discovered that by blending saturated and unsaturated lower alkyl fatty acid esters in the reaction mixture, heterogeneous alkyl glycoside fatty acid polyesters can be produced which do not exhibit undesired anal leakage of the type described below. At least 25% of the lower alkyl fatty acid esters in the reaction mixture must be derived from saturated fatty acids having 12 or more carbons in order to produce a heterogeneous alkyl glycoside fatty acid polyester which does not exhibit anal leakage. It is believed that a substantial portion of the alkyl glycoside molecules contain both saturated and unsaturated fatty acids in the final product. These alkyl glycoside fatty acid polyesters are to be distinguished from the mixed high melting and low melting point alkyl glycoside fatty acid polyester compounds described below.

An alternative alkyl glycoside fatty acid polyester composition suitable for use as a fat substitute food composition is a mixture of low melting point and high melting point alkyl glycoside fatty acid polyesters. Examples of preferred fatty acids suitable for producing low melting point alkyl glycoside fatty acid polyester compounds are C14 to C18 unsaturated fatty acids. Equivalent low melting point compounds are produced from sources that produce mixtures of saturated and unsaturated fatty acids. Examples of such compounds are ethyl glucoside fatty acid polyesters from peanut oil FAME. By low melting point alkyl glycoside fatty acid polyester as used herein is meant those alkyl glycoside fatty acid polyesters which are liquid at room temperature.

Preferred high melting point alkyl glycoside fatty acid polyester compounds of the present invention are composed of fatty acid esters in which the fatty acid moiety is saturated fatty acid having from 12 to 18 carbons. Examples of preferred high melting point alkyl glycoside fatty acid polyester compounds are: methyl glucoside tetralaurate, ethyl glucoside tetramyristate, ethyl galactoside tetrapalmitate and ethyl glucoside tetrastearate. By high melting point alkyl glycoside fatty acid polyester as used herein is meant those alkyl glycoside fatty acid polyesters which are solid at temperatures above 37° C.

It has been discovered that alkyl glycoside fatty acid polyesters that have a melting point of about 37° C. or higher can act as anti-anal leakage agents (AAL) of the type described by Jandacek, U.S. Pat. No. 4,005,195. Accordingly, an effective amount of these glycoside AAL agents can be blended with low melting point alkyl glycoside fatty acid polyesters to produce fat substitute food compositions which are oils at ambient temperature but which do not exhibit the undesirable anal leakage side effect observed when homogeneous low melting point glycoside fatty acid polyesters are used as low calorie fat substitutes alone. Suitable alkyl glycoside fatty acid polyester AAL agents are produced by interesterification of lower acyl ester glycosides with lower alkyl fatty acid esters wherein the fatty acid moiety of the lower alkyl fatty acid ester is a saturated fatty acid having from 14 to 18 carbon atoms. Preferred saturated fatty acids are palmitic and stearic acid. Equivalent glycoside AAL agents are produced by the interesterification of lower alkyl fatty acid esters with blends of lower alkyl fatty acid esters wherein the fatty acid moiety is predominantly saturated with lesser amounts of unsaturated fatty acids. The critical property of the resultant glycoside AAL agent being only that it have a melting point higher than 37°.

Examples of low calorie fat substitute food compositions of the present invention which do not exhibit the undesired anal leakage side effects are provided in Table I below.

TABLE I

| Low Melting Point Alkyl Glycoside Fatty Acid Polyester | High Melting Alkyl Glycoside Fatty Acid Polyester AAL Agent |
|---|---|
| Ethyl glucoside tetraoleate | Ethyl glucoside tetrapalmitate |
| Ethyl galactoside fatty acid polyester of peanut oil FAME | Ethyl glucoside tetrapalmitate |
| Ethyl 4'-galactosyl lactoside fatty acid polyester | Ethyl glucoside tetrapalmitate |
| n-octylglucoside fatty acid polyester of peanut oil FAME | Ethyl galactoside tetrastearate |
| Ethyl glycoside fatty acid polyester of peanut oil FAME | Ethyl galactoside tetrastearate |
| Ethyl lactoside fatty acid polyester of peanut oil FAME | Ethyl lactoside octastearate |

The amount of AAL agent to be blended with low melting point glycoside fatty acid polyester, is known to those skilled in the art and depends upon the amount of low calorie fat substitute composition consumed. It is preferred, that from about 5% to about 50% of the fat ingredients in the fat substitute food composition consist essentially of a high melting point alkylglycoside fatty acid polyester.

The following examples are intended to be illustrative of the present invention and to teach one of ordinary skill how to make and use the invention. These examples are not intended in any way to limit the invention or otherwise limit the protection afforded by Letters Patent hereon.

EXAMPLE I

Methyl oleate (51 g, 0.1720 mole) is placed in a three-necked, round-bottomed flask equipped with a magnetic stirrer, stopcocks, a vacuum take-off line leading to a liquid nitrogen cold trap, manometer, two condensers, thermometers, a vacuum pump and purged with dry $N_2$ gas for 30 min. Ethyl 4'-galactosyl lactose decaacetate (15 g, 0.0155 mole) is added and the $N_2$ purging is continued for an additional 15 min. The mole ratio of methyl oleate to ethyl 4'-galactosyl lactose decaacetate is 11:1. Sodium metal (2% of the reactants by weight, 1.3 g) is added. Heating is started with continuous stirring under dry nitrogen atmosphere. The reaction mixture is heated to 110° C. to 115° C. and pressure is maintained at 0 to 8 mm torr. Synthesis of alkyl glycoside polyesters requires constant dispersion of liquid sodium, liquid ethyl 4'-galactosyl lactose decaacetate and liquid fatty acid methyl esters for optimal interesterification under $N_2$ gas. Interesterification is assumed to begin when catalytic sodium metal and ethyl 4'-galactosyl lactose decaacetate melts and the reaction mixture become homogeneous. Interesterification is continued under constant conditions for two and one-half hours. Volatile methyl acetate is condensed on a liquid nitrogen Dewer column to drive the reaction towards ethyl 4'-galactosyl lactose esterification. Ethyl 4'-galactosyl lactose polyoleate is purified by a modification of the method of Hamm, *J. Food Sci.* 49:419 (1984). The crude ethyl 4'-galactosyl lactose polyoleate reaction mixture is neutralized with $1 \geqq 3$ ml of acetic acid, dissolved in hexane, stirred and bleached with activated charcoal. The reaction mixture is then filtered with Whatman No. 4 filter paper to remove charcoal particles, and the filtrate is washed with 6×400 ml aliquots of methanol allowing enough time for separation. The more dense methanol insoluble layer containing ethyl 4'-galactosyl lactose polyoleate is separated, dried over anhydrous sodium sulfate and filtered with Whatman No. 4 filter paper. Methanol and hexane are then evaporated from ethyl 4'-galactosyl lactose polyoleate. The color of the polyester is golden yellow, similar to corn oil.

EXAMPLE II

The procedure of Example I is repeated substituting 63.26 g of soybean oil FAME for methyl oleate. The average molecular weight of soybean FAME is assumed to be about 278.01. Ethyl 4'-galactosyl lactose decaacetate (20 g, 0.0207 mole) is added to the soybean FAME. An ethyl 4'-galactosyl lactose polyester of soybean oil is produced.

EXAMPLE III

The procedure of Example I is repeated by combining methyl stearate (8.04 g), safflower oil FAME (32.16 g), ethyl 4'-galactosyl lactose decaacetate (12.00 g) and 2% by weight Na (1.04 g). An ethyl 4'-galactosyl lactose polyester of 80:20 (w/w) blend of safflower oil FAME and methyl stearate is produced.

EXAMPLE IV

Substantially anhydrous methyl stearate (4.34 g), safflower oil fatty acid methyl ester (FAME) (39.06 g), and ethyl lactoside heptaacetate (12.5 g) are mixed with 2% by weight Na (1.12 g), based on the weight of the reactants. Interesterification is carried out under dry $N_2$ atmosphere by first gradually heating the reaction mixture to a temperature in the range of 105° C. to 110° C. and maintaining that temperature for two hours. The pressure over the reaction vessel is maintained at 0 to 5 torr. The mole ratio of the fatty acid methyl esters to ethyl lactoside heptaacetate is 8:1. An ethyl lactoside fatty acid polyester of 90:10 (w/w) blend of safflower oil FAME and methyl stearate is produced. The crude methyl lactoside fatty acid polyester is purified as described in Example I.

The foregoing procedure is repeated, except the safflowre oil FAME and methyl stearate blend is replaced by an equivalent amount of safflower oil FAME alone. Ethyl lactoside fatty acid polyester of safflower oil FAME is produced.

EXAMPLE V

Substantially anhydrous methyl oleate 97% pure (69.9 g, 0.2358 mole) and ethyl maltoside heptaacetate (20g, 0.0294 mole) and 2% Na (1.8 g) are mixed. Interesterification is carried out at 105° C. to 110° C. for two and one-half hours under the conditions set forth in Example I. The final mole ratio of methyl oleate to ethyl maltoside heptaacetate is 8:1.

EXAMPLE VI

Substantially anhydrous soybean oil FAME (0.2947 mole) and ethyl lactoside heptaacetate (0.0368 mole) are mixed with 2% by weight sodium metal (2.1 g). The mole ratio of soybean oil FAME to ethyl lactoside heptaacetate is 8:1. Interesterification is performed under dry $N_2$ atmosphere at 115° C. to 118° C. for three hours. The pressure is maintained at 0 to 5 torr. Purification of the crude ethyl lactoside polyester is performed essentially as described in Example 1.

EXAMPLE VII

In a 1000 ml three-necked flask equipped with an efficient stirrer and a thermometer, 40 ml acetic anhydride is cooled in an ice and $H_2O$ mixture. 20 mls of conc. $H_2SO_4$ is added to the mixture dropwise. The solution is warmed to room temperature and 100.0 g of anhydrous D-glucose is added to the stirred mixture, over a ½ hour period. The reaction temperature is maintained between 30° and 40°. Red phosphorus (30 g) is added after cooling the mixture to 20°, followed by the addition of 180 g bromine (58 ml) at a rate sufficient to keep the reaction temperature below 20°. Water (3.6 ml) is added dropwise to the continuously stirred and cooled mixture over about a ½ hour period to prevent the temperature from rising over 20°. The reaction mixture is kept at room temperature for 2 hours. Methylene chloride (300 ml) is then added, and the mixture is filtered through fine glass wool. The reaction flask and filter funnel are washed with 50 ml $CH_2Cl_2$. The filtrate is poured into 80 ml $H_2O$ (near 0°) contained in a separatory funnel. After washing, the $CH_2Cl_2$ layer is drawn off into another separatory funnel which contains 30 ml 0° $H_2O$. The operation is repeated by adding 5 ml $CH_2Cl_2$ to the original aqueous mixture and combining the $CH_2Cl_2$ extracts. After vigorous shaking, the $CH_2Cl_2$ layer is poured into 50 mls of a stirred saturated aqueous solution of sodium hydrogen carbonate pH 6.0. The $CH_2Cl_2$ layer is then dried with $NaSO_4$, and the mixture is filtered. The crystalline mass is admixed with ethanol in the presence of an equimolar amount of $Ag_2CO_3$ and maintained at a temperature of 30°-40° for 2 hours. The crude ethyl glucoside tetraacetate is crystallized from $CH_2Cl_2$ as described above, to produce substantially pure ethyl glucoside tetraacetate.

EXAMPLE VIII

D-galactose is substituted for D-glucose in the reaction mixture described in Example VII. Ethyl galactoside tetraacetate is recrystallized from methylene chloride.

EXAMPLE IX

4'-galactosyl lactose is prepared by adding 1200 g lactose to a 10 liter jar fermentor containing 6 liters of a *Cryptococcus laurentii* broth containing neopepetone (10 g/l) and dextrose (20 g/l) at pH 5.6. The broth containing lactose is incubated at 25°–30° C. for 6 hrs, after which it is centrifuged to remove the microorganisms. The eluate is chromatographed on an activated carbon column, concentrated, filtered and the 4'-galactosyl lactose is crystallized from ethanol.

EXAMPLE X 30 g of 4'-galactosyl lactose produced as described in Example IX is substituted for the D-glucose in the reaction mixture described in Example VII. Interesterification of the acetylated glycoside with methyl oleate is carried out by the method of Example I yielding ethyl 4'-galactosyl lactoside polyoleate.

EXAMPLE XI 20 g of D-lactose is substituted for the D-glucose described in Example VII. Interesterification of the ethyl lactoside heptaacetate with methyl oleate is conducted according to the method of Example I yielding ethyl lactoside polyoleate.

DEEP FAT FRYING

EXAMPLE XII

Low calorie potato chips are produced by frying thin potato slices in ethyl lactoside polyoleate. For each chip a 5 g aliquot of ethyl lactoside polyoleate is poured into a small glass cooking vessel and heated to approximately 360° F. Small potato slices having a thickness of 2 to 3 mm and a diameter of 2 to 3 cm are added to the oil and fried until done.

EXAMPLE XIII

Low calorie potato chips are produced by the method of Example XII by substituting ethyl glycoside tetraester for the ethyl lactoside polyoleate. The ethyl glucoside tetraester is produced by reacting ethyl glucoside tetraacetate, ethyl myristate and ethyl oleate in a ratio of 1:2:6 according to the method of Example I.

EXAMPLE XIV

Low calorie potato chips are produced by frying thin potato slices in ethyl glucoside polyester frying oil. For each potato chip, a 4 g aliquot of ethyl glucoside tetraoleate is combined with a 1 g aliquot of ethyl glucoside tetrapalmitate and the resulting mixture is poured into a small glass cooking vessel and heated to approximately 360° F. Small potato slices, having a thickness of 2 to 3 mm and a diameter of 2 to 3 cm are added to the oil and fried until done. Low calorie potato chips produced in this way have satisfactory texture.

EXAMPLE XV

The procedure described in Example XIV is employed to produce low calorie potato chips by substituting the same quantity of ethyl galactoside fatty acid polyester of peanut oil FAME for ethyl glucoside tetraoleate in the frying oil.

EXAMPLE XVI

The procedure described in Example XIV is employed to produce low calorie potato chips by substituting the same quantity of ethyl lactoside heptastearate for ethyl glucoside tetrapalmitate in the frying oil. These low calorie potato chips have satisfactory texture and flavor.

EXAMPLE XVII

The procedure described in Example XIV is employed to produce satisfactory low calorie potato chips by substituting the same quantity of ethyl glucoside fatty acid polyester of peanut oil FAME for ethyl glucoside tetraoleate in the frying oil.

EXAMPLE XVIII

The procedure described in Example XIV is employed to produce satisfactory low calorie potato chips by substituting the same quantiy of ethyl 4'-galactosyl lactoside fatty acid polyester for methyl glucoside tetraoleate in the frying oil.

SPOONABLE WHITE SALAD DRESSING

EXAMPLE XIX

A low calorie spoonable white salad dressing is prepared by replacing the oil in a typical recipe of this type with ethyl 4'-galactosyl lactose fatty acid polyester prepared from safflower oil FAME. Mixing the ingredients in the proportions below produced a salad dressing with satisfactory consistency and taste.

| Ingredient | Percent by Weight |
| --- | --- |
| Ethyl 4'-galactosyl lactose fatty acid polyester | 30.0 |
| Starch paste | 60.0 |
| starch | |
| sugar | |
| salt | |
| vinegar | |
| water | |
| Egg yolk | 5.0 |
| Water | 3.9 |
| Vinegar | 1.0 |
| Gum | 0.1 |
| | 100 |

EXAMPLE XX

A low calorie spoonable white salad dressing is prepared by replacing the oil in a typical recipe of this type with ethyl glucoside polyesters. Mixing the ingredients in the proportions below produced a salad dressing with satisfactory consistency and taste.

| Ingredient | Percent by Weight |
| --- | --- |
| Ethyl glucoside tetraoleate | 20.0 |
| Ethyl glucoside tetrapalmitate | 10.0 |
| Starch paste | 60.0 |
| starch | |
| sugar | |
| salt | |
| vinegar | |
| water | |
| Egg yolk | 5.0 |
| Water | 3.9 |
| Vinegar | 1.0 |
| Gum | .1 |
| | 100.0 |

EXAMPLE XXI

The ingredients in Example XX are employed to produce a satisfactory low calorie spoonable white salad dressing by substituting the same quantity of ethyl glucoside fatty acid polyester of peanut oil FAME for ethyl glucoside tetraoleate in the oil.

EXAMPLE XXII

The ingredients in Example XX are employed to produce a satisfactory low calorie spoonable white salad dressing by substituting the same quantity of ethyl galactoside tetrastearate for ethyl glucoside tetrapalmitate in the oil.

EXAMPLE XXIII

The ingredients in Example XX are employed to produce a satisfactory low calorie spoonable white salad dressing by substituting the same quantity of ethyl 4'-galactosyl lactoside fatty acid polyester for ethyl glucoside tetraoleate in the oil.

ITALIAN SALAD DRESSING

| Ingredient | Percent by Weight |
| --- | --- |
| Ethyl 4'-galactosyl lactose fatty acid polyester | 40.00 |
| Water | 35.45 |
| Lemon juice | 5.80 |
| Vinegar (120 grain) | 13.00 |
| Salt | 3.5 |
| Starch | 0.80 |
| Garlic | 2.00 |
| Onion and garlic | 1.00 |
| Other spices | 0.25 |
|  | 100.00 |

EXAMPLE XXIV

A low calorie Italian salad dressing is prepared by replacing the oil found in typical recipoes of this type with ethyl 4'-galactosyl lactose fatty acid polyester prepared from safflower FAME as described in Example III.

EXAMPLE XXV

Low calorie salad dressing is produced by substituting the same percent by weight of ethyl lactoside fatty acid polyester prepared as described in Example VII for the ethyl 4'-galactosyl lactose fatty acid polyester in the salad dressing recipe of Example XXIV.

EXAMPLE XXVI

A low calorie Italian salad dressing is prepared by replacing the oil found in typical recipes of this type with ethyl glucoside polyester prepared from safflower FAME as described in Example XIV, and the glycoside AAL agent ethyl lactoside heptastearate.

| Ingredient | Percent by Weight |
| --- | --- |
| Ethyl glucoside tetraoleate | 30.00 |
| Ethyl lactoside neptastearate | 10.00 |
| Water | 35.45 |
| Lemon juice | 5.80 |
| Vinegar (120 grain) | 13.00 |
| Salt | 3.50 |
| Starch | .80 |
| Garlic | 2.00 |
| Onion and garlic | 1.00 |
| Other spices | .25 |
|  | 100.00 |

EXAMPLE XXVII

Low calorie salad dressing is produced by substituting the same percent by weight of ethyl galactoside tetraoleate prepared as described above for the ethyl glucoside tetraoleate in the salad dressing recipe of Example XXIII.

All of the alkyl glycoside fatty acid polyesters produced in accordance with the present invention are usable as substitutes for naturally occurring fats and oils. The process and the novel products produced have been described in conjunction with preferred embodiments. One of ordinary skill, after reviewing the foregoing specification, will be able to make various changes, substitutions of equivalents, and other alterations without deparing from the broad concepts disclosed herein. It is therefore intended that protection afforded by Letters Patent hereon be limited only by the definition contained in the appended claims and equivalents thereof.

While the preferred embodiment of the invention has been described, other modifications may be made thereto and other embodiments may be devised within the spirit of the invention and scope of the appended claims.

The embodiments of the invention in which an exclusive property or privilege is claimed are defined as follows:

1. A low calorie food composition comprising: nonfat ingredients, and
fat ingredients, wherein from about 5.0% to about 95% of the fat ingredients comprises an alkyl glycoside fatty acid polyester having at least four fatty acid ester groups,
wherein the fatty acid ester groups comprise both saturated and unsaturated fatty acid ester groups, each fatty acid having from 4 to 24 carbon atoms, and
wherein the alkyl glycoside moiety comprises a saccharide portion and an alkyl portion, the alkyl portion having from 1 to 24 carbon atoms.

2. The composition of claim 1, wherein the saccharide portion is selected from the group consisting of: fructose, glucose, galactose, mannose, ribulose, rhaminose, xylose, xylulose, ribose, arabinose, sorbose, maltose, lactose, cellobiose, melibiose, adn 4'-galactosyl lactose.

3. The composition of claim 2, wherein the saccharide portion is glucose or galactose.

4. The composition of claim 1, wherein the alkyl portion is selected from the group consisting of: methyl, ethyl, n-propyl, n-butyl, n-pentyl, n-octyl, n-decyl, n-dodecyl, n-tetradecyl, n-hexadecyl, and n-octadecyl.

5. The composition of claim 1, wherein the alkyl portion is ethyl or n-propyl.

6. A low calorie food composition comprising: nonfat ingredients and fat ingredients wherein from about 5.0% to about 95% of the fat ingredients comprises: (a) a low melting point alkyl glycoside fatty acid polyester compound wherein the compound has at least four fatty acid ester groups, each fatty acid having from 4 to 24 carbon atoms; and (b) an effective amount of a high melting point alkyl glycoside fatty acid polyester having at least four fatty acid ester groups, each fatty acid having from 4 to 24 carbons, to prevent anal leakage of the compound.

7. The composition of claim 6, wherein from about 5% to about 50% of the fat ingredients comprises the high melting point alkyl glycoside fatty acid polyester.

* * * * *

UNITED STATES PATENT AND TRADEMARK OFFICE
CERTIFICATE OF CORRECTION

PATENT NO. : 4,840,815

DATED : June 20, 1989

INVENTOR(S) : Richard S. Meyer, Jeffrey M. Root, Michael L. Campbell, Daryl B. Winter It is certified that error appears in the above-identified patent and that said Letters Patent is hereby corrected as shown below:

Column 2, line 64: "3,722,269" should be --3,772,269--
Column 3, line 10: "means" should be --meant--
Column 3, line 17: "alchohols" should be --alcohols--
Column 3, line 58: "froma bout" should be --from about--
Column 4, line 63: "homogenous" should be --homogeneous--
Column 5, line 15: "ingredents" should be --ingredients--
Column 5, line 64: after "is" insert --a--
Column 6, line 55: "alkylglycoside" should be --alkyl glycoside--
Column 7, line 25: "1⅔ ml" should be --1-3 ml--
Column 8, lines 3-4: "safflowre" should be --safflower--
Column 11, lines 22-42: the table entitled "Italian Salad Dressing" should be situated after Example XXIV
Column 11, line 38: "recipoes" should be --recipes--
Column 12, line 16: "deparing" should be --departing--
Column 12, line 44: "adn" should be --and--

Signed and Sealed this

Tenth Day of July, 1990

Attest:

HARRY F. MANBECK, JR.

Attesting Officer

Commissioner of Patents and Trademarks

REEXAMINATION CERTIFICATE (3340th)

United States Patent [19]
Meyer et al.

[11] B1 4,840,815
[45] Certificate Issued Sep. 30, 1997

[54] LOW CALORIC ALKYL GLYCOSIDE POLYESTER FAT SUBSTITUTES

[75] Inventors: Richard S. Meyer; Jeffrey M. Root, both of Tacoma; Michael L. Campbell, Kent; Daryl B. Winter, Seattle, all of Wash.

[73] Assignee: Curtis-Burns, Inc., Rochester, N.Y.

Reexamination Request:
No. 90/002,670, Mar. 11, 1992

Reexamination Certificate for:
Patent No.: 4,840,815
Issued: Jun. 20, 1989
Appl. No.: 122,188
Filed: Nov. 18, 1987

Certificate of Correction issued Jul. 10, 1990.

Related U.S. Application Data

[63] Continuation-in-part of Ser. No. 49,625, May 13, 1987, abandoned.

[51] Int. Cl.$^6$ ............................................. A23D 5/00
[52] U.S. Cl. ...................... 426/611; 426/601; 426/804; 536/4.1
[58] Field of Search .................. 426/601, 611, 426/804; 536/4.1

[56] References Cited

U.S. PATENT DOCUMENTS

| | | | |
|---|---|---|---|
| 2,759,923 | 8/1956 | Gibbons | 260/210 |
| 2,831,854 | 4/1958 | Tucker et al. | 260/234 |
| 2,931,797 | 4/1960 | Gibbons et al. | 260/210 |
| 3,096,324 | 7/1963 | Goins et al. | 260/234 |
| 3,219,656 | 11/1965 | Boettner | 260/210 |
| 3,248,381 | 4/1966 | Nobile et al. | 260/234 |
| 3,249,600 | 5/1966 | Nobile et al. | 260/234 |
| 3,251,827 | 5/1966 | Schnell et al. | 260/234 |
| 3,347,848 | 10/1967 | Ismail et al. | 260/234 |
| 3,547,828 | 12/1970 | Mansfield et al. | 252/351 |
| 3,558,597 | 1/1971 | von Brachel et al. | 260/234 |
| 3,597,417 | 8/1971 | Myhre | 260/234 |
| 3,598,865 | 8/1971 | Lew | 260/210 R |
| 3,600,186 | 8/1971 | Mattson et al. | 426/601 |
| 3,625,706 | 12/1971 | Myhre | 99/94 |
| 3,634,397 | 1/1972 | Thompson et al. | 260/234 R |
| 3,707,535 | 12/1972 | Lew | 260/210 R |
| 3,714,144 | 1/1973 | Feuge et al. | 260/234 R |
| 3,729,461 | 4/1973 | Pomeranz et al. | 260/210 R |
| 3,772,269 | 11/1973 | Lew | 260/210 R |
| 3,839,318 | 10/1974 | Mansfield | 260/210 R |
| 3,893,990 | 7/1959 | Hass et al. | 260/234 |
| 3,963,699 | 6/1976 | Rizzi et al. | 260/234 R |
| 4,005,195 | 1/1977 | Jandacek | 424/180 |
| 4,349,669 | 9/1982 | Klahr et al. | 536/127 |
| 4,368,213 | 1/1983 | Hollenback et al. | 426/590 |
| 4,382,924 | 5/1983 | Berling et al. | 424/180 |
| 4,461,782 | 7/1984 | Robbins et al. | 426/549 |
| 4,517,360 | 5/1985 | Volpenhein | 536/119 |
| 4,518,722 | 5/1985 | Volpenhein | 536/119 |
| 4,610,889 | 9/1986 | Schmidt | 426/602 |
| 4,611,055 | 9/1986 | Yamamoto et al. | 536/119 |
| 4,713,447 | 12/1987 | Letton | 536/186 |
| 4,721,781 | 1/1988 | Rowton | 536/4.1 |
| 4,797,300 | 1/1989 | Jandacek et al. | 426/549 |
| 4,810,516 | 3/1989 | Kong-Chan | 426/548 |
| 4,840,815 | 6/1989 | Meyer et al. | 425/611 |
| 4,952,687 | 8/1990 | Bodor et al. | 536/119 |

FOREIGN PATENT DOCUMENTS

| | | |
|---|---|---|
| 0233856 | 2/1987 | European Pat. Off. . |
| 0236288 | 2/1987 | European Pat. Off. . |
| 0254376 | 1/1988 | European Pat. Off. ........ C07H 13/06 |
| 0256585 | 2/1988 | European Pat. Off. ........ C07H 13/06 |
| 0301634 | 2/1989 | European Pat. Off. ........ C07H 13/06 |
| 0304130 | 2/1989 | European Pat. Off. ........ A23D 3/00 |
| 0304131 | 2/1989 | European Pat. Off. ........ A23D 3/00 |
| 156263 | 9/1982 | German Dem. Rep. . |

OTHER PUBLICATIONS

The American Heritage Dictionary 1982 Houghton Mifflin Company pp. 491 and 864.

Mattson et al., "Hydrolysis of Fully Esterified alcohols containing from one to eight hydroxyl groups by the lipolytic enzymes of rat pancreatic juice" Journal of Lipid Research vol. 13 pp. 325–328 1972.

D.J. Hamm, "Preparation and Evaluation of Trialkoxytricarballylate, Trialkoxycitrate, Trialkoxyglycerlether, Jojoba Oil and Sucrose Polyester as Low Calories Replacements of Edible Fats and Oils," Journal of Food Science, vol. 49 (1984).

"Food Fats and Oils," Institute of Shortening and Edible Oils, Inc., pp. 4, 5, & 21 (Jan. 1988).

A. Streitwiesir, Jr. et al., "Introduction to Organic Chemistry," Macmillan Pub. Co. Inc., New York, pp. 506–507 (1976).

Primary Examiner—Carolyn Paden

[57] ABSTRACT

Alkyl glycoside fatty acid polyesters having at least four fatty acid ester groups being both saturated and unsaturated and having 4 to 24 carbon atoms wherein the alkyl glycoside moiety comprises a saccharide and an alkyl portion are suitable for use as a low calorie fat substitute food composition.

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–7 are cancelled.

* * * * *